(12) United States Patent
Hendriks et al.

(10) Patent No.: US 12,374,445 B2
(45) Date of Patent: Jul. 29, 2025

(54) MECHANICAL VENTILATOR CONFIGURATION FOR MECHANICAL VENTILATION OF A PATIENT WITH LIMITED OR NO IMAGING DATA OF THE PATIENT

(71) Applicant: KONINKLIJKE PHILIPS N.V., Eindhoven (NL)

(72) Inventors: Cornelis Petrus Hendriks, Eindhoven (NL); Roberto Buizza, Eindhoven (NL); Michael Polkey, London (GB); Joerg Sabczynski, Hamburg (DE); Rafael Wiemker, Hamburg (DE); Jaap Roger Haartsen, Eindhoven (NL); Thomas Koehler, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 351 days.

(21) Appl. No.: 18/129,921

(22) Filed: Apr. 3, 2023

(65) Prior Publication Data
US 2023/0402157 A1 Dec. 14, 2023

Related U.S. Application Data

(60) Provisional application No. 63/350,435, filed on Jun. 9, 2022.

(51) Int. Cl.
*G16H 30/40* (2018.01)
*A61M 16/00* (2006.01)

(52) U.S. Cl.
CPC .......... *G16H 30/40* (2018.01); *A61M 16/024* (2017.08); *G06T 2207/10* (2013.01)

(58) Field of Classification Search
None
See application file for complete search history.

(56) References Cited

U.S. PATENT DOCUMENTS

| 8,812,431 B2 | 8/2014 | Voigt | |
|---|---|---|---|
| 2011/0191283 A1 | 8/2011 | Voigt | |
| 2023/0201504 A1* | 6/2023 | Varga | A61M 16/026 128/204.23 |

OTHER PUBLICATIONS

International Search Report for PCT/EP2023/064473 filed May 31, 2023.

(Continued)

*Primary Examiner* — Lennin R Rodriguezgonzalez
(74) *Attorney, Agent, or Firm* — Daniel H. Brean (57) ABSTRACT

A non-transitory storage medium stores instructions readable and executable by at least one electronic processor to receive clinical data for a current patient (P); search a database of CT scans and/or patient-specific mechanical ventilation models for other patients using the clinical data for the current patient as a search criterion to identify a similar patient in the database and similar patient data (S) comprising a CT scan and/or a patient-specific mechanical ventilation model for the similar patient; determine a patient-specific mechanical ventilation model for the current patient based on the CT scan and/or patient-specific mechanical ventilation model for the similar patient; generate ventilator configuration data for mechanically ventilating the current patient based on the determined patient-specific mechanical ventilation model for the current patient.

14 Claims, 3 Drawing Sheets

(56) References Cited

OTHER PUBLICATIONS

Roth, C.J. et al., 2017, "A comprehensive computational human lung model incorporating inter-acinar dependencies: Application to spontaneous breathing and mechanical ventilation", Int. J. Numer. Metho. Biomed. Engng. (2017); e02787.

Parimbelli, E. et al., 2018. "Patient similarity for precision medicine: A systematic review." Journal of Biomedical Informatics, vol. 83, 2018, pp. 87-96.

Wang, Y. et al. 2019. "DeepOrganNet: on-the-fly reconstruction and visualization of 3D/4D lung models from single-view projections by deep deformation network." IEEE Transactions on Visualization and computer graphics. pp. 1-1.

Huang, H-Z et al., "Heterogeneous Information Network-Based Patient Similarity Search." Front. Cell Dev. Biol. 9:735687. (2021).

Sharafoddini, A. et al., (2017), "Patient similarity in prediction models based on health data: a scoping review", JMIR Med Inform 2017;5(1):e7.

* cited by examiner

MECHANICAL VENTILATOR CONFIGURATION FOR MECHANICAL VENTILATION OF A PATIENT WITH LIMITED OR NO IMAGING DATA OF THE PATIENT

CROSS-REFERENCE TO RELATED APPLICATIONS

This patent application claims the priority benefit under 35 U.S.C. § 119(e) of U.S. Provisional Application No. 63/350,435, filed on Jun. 9, 2022, the contents of which are herein incorporated by reference.

The following relates generally to mechanical ventilators, the mechanical respiratory therapy arts, mechanical ventilator configuration or setup, respiratory stress and strain arts, Ventilator Induced Lung Injury (VILI) prevention arts, and related arts.

BACKGROUND

During mechanical ventilation therapy of a patient, clinicians decide the volume of air (e.g. per breath) that a mechanical ventilator is to provide to the patient based on body size of the patient. This volume needs to provide sufficient aeration without causing damage to the lung due to stress (barotrauma), strain (volutrauma), or shear due to cyclic opening and collapse of the alveoli (atelectrauma). This type of lung damage due to the stresses and strains imposed by the mechanical ventilator is known as Ventilator Induced Lung Injury (VILI).

A problem in determining the mechanical ventilator settings for preventing lung damage is that the lung is heterogeneous, either intrinsically due to locally varying structures, geometry, and mechanical properties, or secondarily due to local damage or fluid accumulation caused by a disease or infection such as chronic obstructive pulmonary disease (COPD), pneumonia, edema, Covid-19, fibrosis, and so forth. This heterogeneity of the lungs can lead to local stress and strain concentrations that are much higher than the apparent (e.g. average or global) stress and strain, as can be estimated based on the patient's body size, or based on the lumped volume and compliance as measured by sophisticated mechanical ventilators.

In some current approaches, a solution for the assessment and prevention of VILI includes constructing a three-dimensional (3D) biophysical model of a patient's lungs based on computed tomography (CT) exhalation imaging information of the patient (see, e.g., Roth, J. et al., 2017, "A comprehensive computational human lung model incorporating inter-acinar dependencies: Application to spontaneous breathing and mechanical ventilation", Int. J. Numer. Meth. Biomed. Engng. (2017); e02787). With this model constructed using the CT imaging of the patient, the clinician can virtually test various mechanical ventilator (MV) settings and see via simulation what happens in the lung (e.g., a strain distribution in the parenchymal tissue). The mechanical properties of the lung tissue (i.e., the stiffness of the alveolar ducts and the inter alveoli linkers) are chosen such that the lung model simulates experimental behavior. In this approach, the mechanical properties are not patient specific and not locally varying. The model of the patient's lungs generated using the CT images of the patient is sometimes referred to as a digital twin, as it is a digital representation of the physical lungs of the patient.

The following discloses certain improvements.

SUMMARY

In one aspect, a non-transitory storage medium stores instructions readable and executable by at least one electronic processor to receive clinical data for a current patient; search a database of CT scans and/or patient-specific mechanical ventilation models for other patients using the clinical data for the current patient as a search criterion to identify a similar patient in the database and similar patient data comprising a CT scan and/or a patient-specific mechanical ventilation model for the similar patient; determine a patient-specific mechanical ventilation model for the current patient based on the CT scan and/or patient-specific mechanical ventilation model for the similar patient; and generate ventilator configuration data for mechanically ventilating the current patient based on the determined patient-specific mechanical ventilation model for the current patient.

In another aspect, a mechanical ventilation method comprises, with at least one electronic controller receiving clinical data for a current patient; searching a database of CT scans and/or patient-specific mechanical ventilation models for other patients using the clinical data for the current patient as a search criterion to identify a similar patient in the database and similar patient data comprising a CT scan and/or a patient-specific mechanical ventilation model for the similar patient; determining a patient-specific mechanical ventilation model for the current patient based on the CT scan and/or patient-specific mechanical ventilation model for the similar patient; and generating ventilator configuration data for mechanically ventilating the current patient based on the determined patient-specific mechanical ventilation model for the current patient.

One advantage resides in providing a model of the lungs of a patient undergoing mechanical ventilation therapy having mechanical properties with heterogeneous tissue stiffness, patient-specific, and calibrated mechanical properties, without the need for CT images of the patient to provide the basis for constructing the model.

Another advantage resides in providing a model of the lungs of a patient undergoing mechanical ventilation therapy with color-coded tissue map sections corresponding to mechanical properties of the lungs.

Another advantage resides in providing a model of the lungs of a patient undergoing mechanical ventilation therapy on a display device of a mechanical ventilator, thereby reducing the need for an additional computer in an intensive care unit (ICU).

Another advantage resides in providing a model of the lungs of a patient undergoing mechanical ventilation therapy that dynamically updates with additional imaging data of the patient.

Another advantage resides in providing a digital twin of a thoracic cavity of a patient, including the lungs of the patient, undergoing mechanical ventilation therapy that can be used to simulate changes in settings of the mechanical ventilator.

Another advantage resides in developing a digital model of a patient's lungs without the use of CT images.

Another advantage resides in determining when to acquire a new CT scan of a patient and thereby postponing such a scan unless and until necessary.

Another advantage resides in reducing ionizing radiation exposure to a patient undergoing mechanical ventilation therapy.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

As used herein, the singular form of "a," "an," and "the" include plural references unless the context clearly dictates otherwise. As used herein, statements that two or more parts or components are "coupled," "connected," or "engaged" shall mean that the parts are joined, operate, or co-act together either directly or indirectly, i.e., through one or more intermediate parts or components, so long as a link occurs. Directional phrases used herein, such as, for example and without limitation, top, bottom, left, right, upper, lower, front, back, and derivatives thereof, relate to the orientation of the elements shown in the drawings and are not limiting upon the scope of the claimed invention unless expressly recited therein. The word "comprising" or "including" does not exclude the presence of elements or steps other than those described herein and/or listed in a claim. In a device comprised of several means, several of these means may be embodied by the same item of hardware.

CT imaging based digital twin simulations can support decisions on a personalized protective ventilation scenario. However, a prior CT scan might not always be available, for example with a trauma patient or with children or pregnant women when exposure to ionizing radiation should be avoided as much as possible. Furthermore, when a patient has been in the ICU for a while it might be needed to take a new CT scan for diagnostic reasons or to adjust the mechanical ventilation therapy. However, a CT scan with ICU patients, especially, when being sedated, is challenging.

Disclosed herein are systems and methods to support bedside clinicians and care providers in providing safe mechanical ventilation, including guiding clinicians in selecting ventilator settings that will not produce VILI in the specific patient. The disclosed approaches in some embodiments do not require acquisition of CT images of the patient for constructing a digital twin of the patient for use in determining the mechanical ventilator settings.

In construction of a digital twin of a specific patient's lungs, linear or non-linear local lung compliance numbers (relative numbers) are mapped using deformable image registration (DIR) with CT or three-dimensional (3D) or multi-view X-ray images of the patient. Imaging is triggered or timed at zero flow in the breathing cycle to determine absolute pressures without using breath hold or pause maneuvers. Concurrently with the imaging, transpulmonary pressure readings are acquired. Image calibration is performed with mechanical ventilator data to convert the relative lung compliance into absolute numbers. This uses the transpulmonary pressure values. The output of the process is a quantitative elasticity map.

A digital twin of the patient's thoracic cavity, including the lungs, is then generated, i.e., a four-dimensional (4D, space and time dimensions) biophysical lung model including structure, ventilation, and deformation aspects, which is continuously calibrated and updated with mechanical ventilator data and bedside imaging information (e.g., using an imaging modality such as 3D or multi-view X-ray or ultrasound). The digital twin simulates effects in the lungs at different ventilator settings, in particular tissue stress. Input to the lung model is the quantitative elasticity distribution previously acquired.

However, acquiring CT or 3D or multi-view X-ray images of the patient may not be feasible or advisable, for example due to a desire to avoid ionizing radiation exposure of an at-risk patient, difficulty in positioning an unconscious patient, exigency of a clinical emergency situation, or so forth. In these cases, the usual approach for constructing a patient-specific digital twin for configuring the mechanical ventilator is not feasible, due to the lack of access to CT or 3D or multi-view X-ray images of the patient.

In embodiments disclosed herein, this type of situation is addressed by constructing a patient-specific digital twin of the patient's lungs based on CT or 3D or multi-view X-ray imaging data for a similar patient. Alternatively, if a digital twin of a similar patient is available then this digital twin can be directly adjusted to the current patient.

Some embodiments further provide a user interface (UI) with an easily read display. The model output is translated in actionable clinical decision support (CDS) information. The user interface (UI) of the mechanical ventilator shows options for the clinician to decide from.

Figure 1:
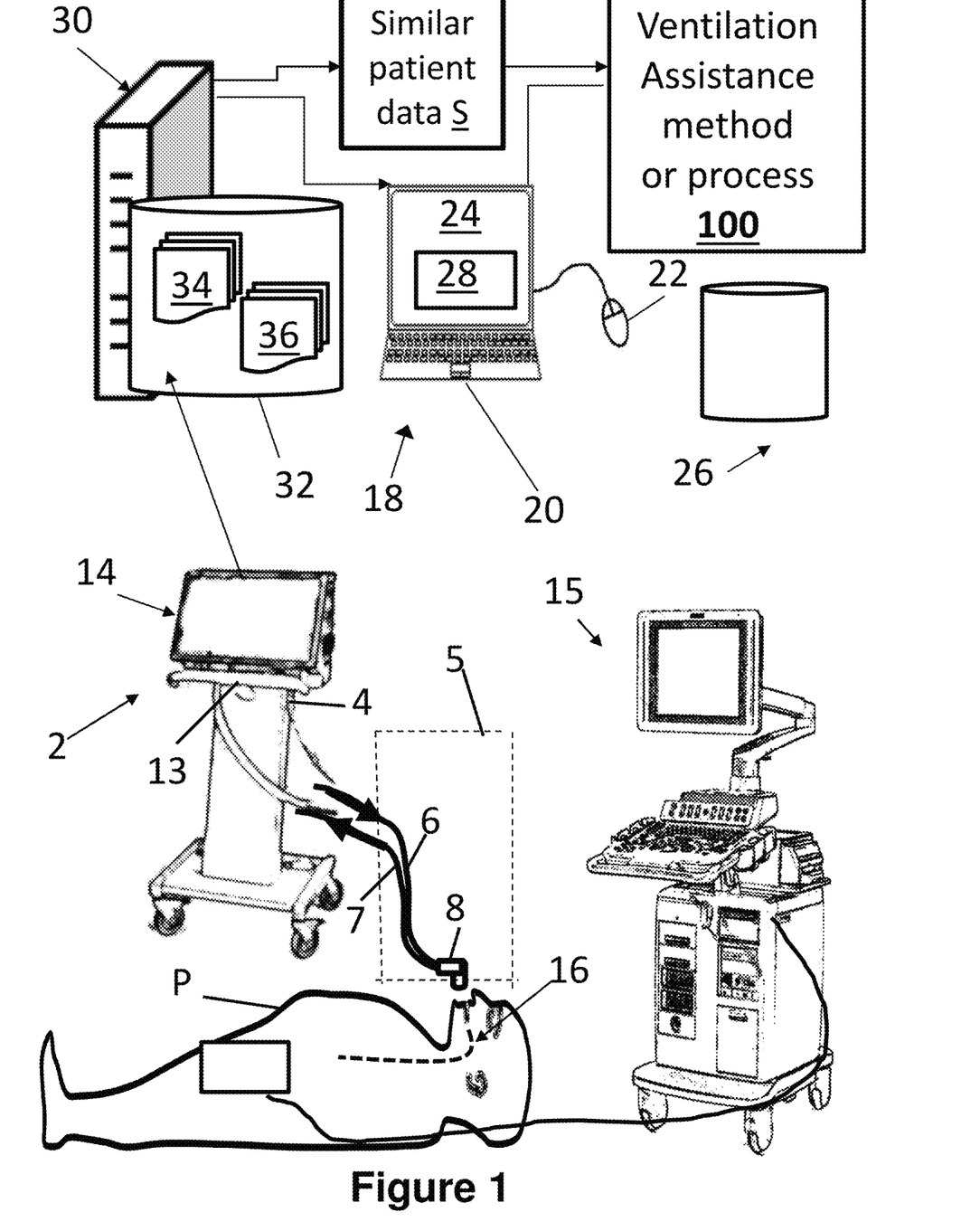
FIG. 1 diagrammatically shows an illustrative mechanical ventilation system in accordance with the present disclosure.

With reference to FIG. 1, a mechanical ventilator 2 for providing ventilation therapy to an associated current patient P is shown. As shown in FIG. 1, the mechanical ventilator 2 includes an outlet 4 connectable with a patient breathing circuit 5 to delivery mechanical ventilation to the current patient P. The patient breathing circuit 5 includes typical components for a mechanical ventilator, such as an inlet line 6, an optional outlet line 7 (this may be omitted if the ventilator employs a single-limb patient circuit), a connector or port 8 for connecting with an endotracheal tube (ETT), and one or more breathing sensors (not shown), such as a gas flow meter, a pressure sensor, end-tidal carbon dioxide ($etCO_2$) sensor, and/or so forth. The mechanical ventilator 2 is designed to deliver air, an air-oxygen mixture, or other breathable gas (supply not shown) to the outlet 4 at a programmed pressure and/or flow rate to ventilate the patient via an ETT. The mechanical ventilator 2 also includes an electronic controller (e.g., a microprocessor) 13 for controlling operation of the mechanical ventilator 2, and a display device 14 for displaying information about the current patient P and/or settings of the mechanical ventilator 2 during mechanical ventilation of the current patient P.

FIG. 1 diagrammatically illustrates the current patient P intubated with an ETT 16 (the lower portion of which is inside the current patient P and hence is shown in phantom). The connector or port 8 connects with the ETT 16 to operatively connect the mechanical ventilator 2 to deliver breathable air to the current patient P via the ETT 16. The mechanical ventilation provided by the mechanical ventilator 2 via the ETT 16 may be therapeutic for a wide range of conditions, such as various types of pulmonary conditions like emphysema or pneumonia, viral or bacterial infections impacting respiration such as a COVID-19 infection or severe influenza, cardiovascular conditions in which the current patient P receives breathable gas enriched with oxygen, or so forth.

FIG. 1 also shows an optional medical imaging device 15 (also referred to as an image acquisition device, imaging device, and so forth). The image acquisition device 15 can be a two-dimensional (2D) X-ray imaging device or an ultrasound (US) image acquisition device, for example. As primarily described herein, the medical imaging device 15 comprises a US medical imaging device 15 (i.e., a bedside US imaging device). An ultrasound imaging device is a typical choice for a patient who is not a good candidate for CT or 3D or multi-view X-ray imaging due to being at-risk for ionizing radiation exposure, lacks mobility, or requires urgent mechanical ventilation therapy Another option is a 2D X-ray imaging device such as a direct digital radiograph (DDR) imaging device, which acquires a single planar X-ray image of the current patient P.

With continuing reference to FIG. 1, an electronic processing device 18 is shown. The electronic processing device 18 can comprise an electronic processing device, such as a workstation computer (more generally, a computer), a smart device (e.g., a smartphone, a tablet, and so forth), or server computer or a plurality of server computers, (e.g., interconnected to form a server cluster, cloud computing resource, or so forth). The electronic processing device 18 includes typical components, such as an electronic controller 20 (e.g., an electronic processor or a microprocessor), at least one user input device (e.g., a mouse, a keyboard, a trackball, a finger swipe on a touchscreen of a smart device, and/or the like) 22, and at least one display device 24 (shown only in FIG. 1, e.g., an LCD display, plasma display, cathode ray tube display, and/or so forth). In some embodiments, the display device 24 can be a separate component from the electronic processing device 18. The display device 24 may also comprise two or more display devices.

The electronic controller 20 is operatively connected with a one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the ventilation assistance device 18, various combinations thereof, or so forth. It is to be understood that any reference to a non-transitory medium or media 26 herein is to be broadly construed as encompassing a single medium or multiple media of the same or different types. Likewise, the electronic controller 20 may be embodied as a single electronic processor or as two or more electronic processors. The non-transitory storage media 26 stores instructions executable by the at least one electronic controller 20. The instructions include instructions to generate a graphical user interface (GUI) 28 for display on the remote operator display device 24.

FIG. 1 also shows a server computer 30 (e.g., an electronic processor) configured to generate data related to the current patient P and/or settings of the mechanical ventilator 2 during mechanical ventilation of the current patient P. The server computer 30 also includes a database 32 storing a plurality of previously-acquired (i.e., historical) CT scans 34, and/or a plurality of patient-specific mechanical ventilation models 36 for other patients. The patient-specific mechanical ventilation models 36 can comprise, for example, an anatomical model, an artificial neural network (ANN), and so forth.

The patient-specific mechanical ventilation models 36 are also referred to herein as a "digital twin" of the lungs. In some mechanical ventilation therapy sessions, there might be rare instances when there is no CT scan available at ICU admission of a current patient, but it is still desirable to develop and apply a protective ventilation scenario with a digital twin model. Provided with a sufficiently large library of imaging and other clinical data that is available and accessible, the server computer 30 is configured is to search a similar patient, take the digital twin of the similar patient, and personalize this model for the current patient P using the available similar patient data S which is adjusted to the current patient P. The similar patient data S can be, for example, a CT scan and/or a patient-specific mechanical ventilation model for the similar patient. The patient-specific mechanical ventilation models 36 can be a mesh-based model, but do not need to be a mesh-based model. The patient-specific mechanical ventilation models 36 comprise imaging-based patient-specific biophysical models, providing insight in heterogeneous lung deformation and flow. This may include the use of meshless approaches, mathematical models, machine learning, data analytics, etc.

Furthermore, as disclosed herein, the database 32 stores instructions executable by the server computer 30 to perform a mechanical ventilation assistance method or process 100 to provide mechanical ventilation therapy to the current patient P. The mechanical ventilation assistance method or process 100 is directed to a situation in which the current patient P is not amenable to be imaged by a technique such as CT imaging or 3D or multi-view X-ray imaging that provides high resolution imaging data from which a digital model (i.e. digital twin) of the patient's lungs can be constructed. The patient P may however optionally be imaged by an imaging modality or system that does not provide high resolution imaging data from which a digital model can be constructed, but which may be sufficient to provide lower resolution or low granularity information about the patient's lungs or neighboring anatomy, such as the illustrative ultrasound imaging device 15. To overcome the lack of suitable imaging data of the current patient P for constructing a digital twin of the lungs of the current patient P, the mechanical ventilation assistance method or process 100 instead leverages high-resolution imaging data of a similar patient or (if available) an actual digital twin of the similar patient, and adjusts this similar patient data S to create a patient-specific digital twin for the current patient P that is specific to the current patient P. The thusly created patient-specific digital twin for the current patient P is then used to configure the mechanical ventilator 2 for the current patient P, thereby providing patient-specific tailored mechanical ventilator settings in the absence of availability of high resolution CT, 3D or multi-view X-ray, or other like imaging data of the current patient P.

Figure 2:
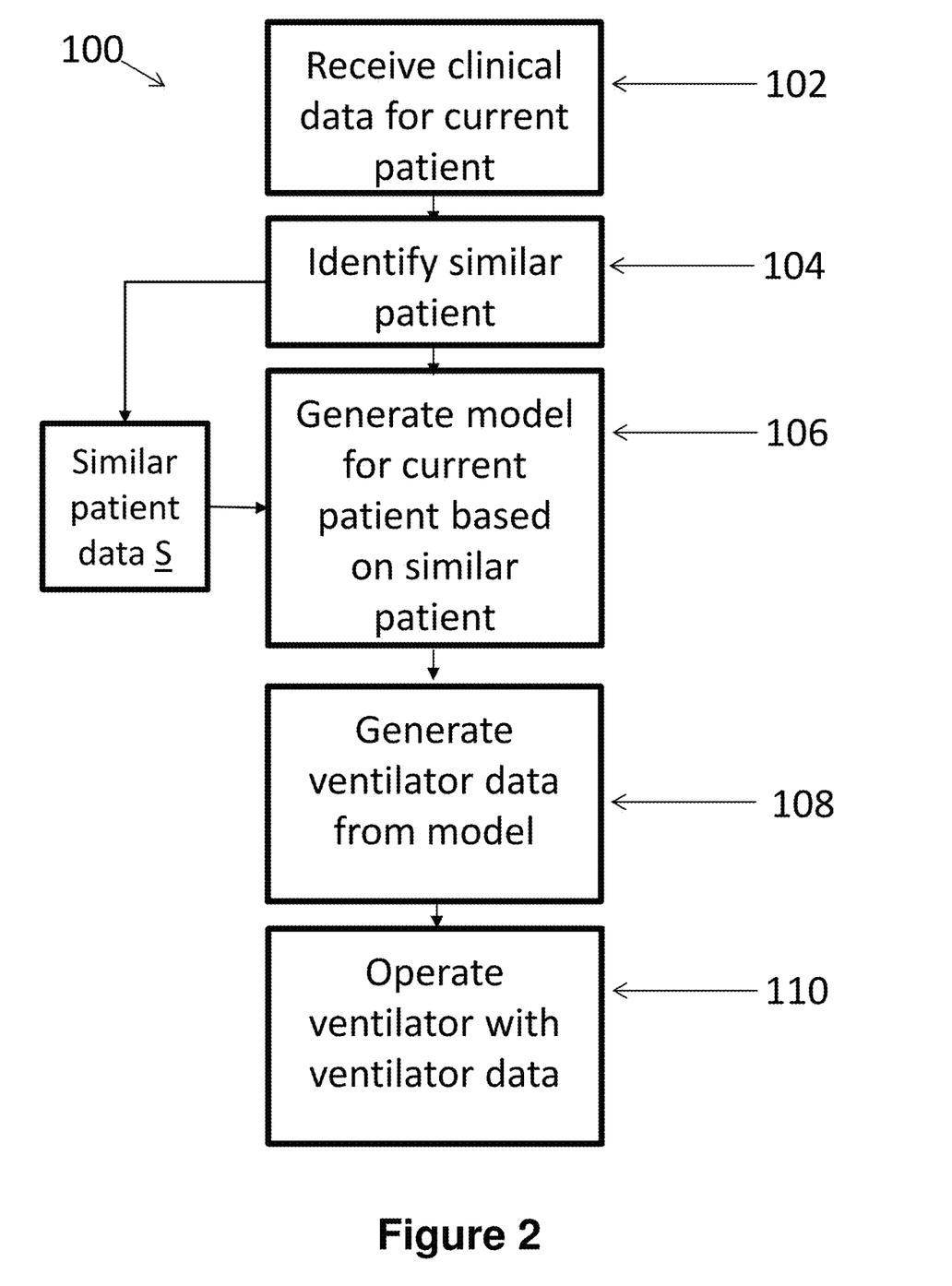
FIG. 2 shows an example flow chart of operations suitably performed by the system of FIG. 1.

With reference to FIG. 2, and with continuing reference to FIG. 1, an illustrative embodiment of the mechanical ventilation assistance method 100 is diagrammatically shown as a flowchart. At an operation 102, clinical data for a current patient is received by the server computer 30. The clinical data can optionally include, for example, imaging data of lungs of the current patient (e.g., two-dimensional (2D) X-ray imaging data, ultrasound imaging data, and so forth), and the imaging data of the lungs of the current patient does not include a computed tomography (CT) scan of the lungs of the current patient P. The received clinical data for the current patient can include clinical data indicative of one or more of: ultrasound or 2D X-ray imaging-derived data such as lung size, lung shape, lung function, and/or non-imaging based data such as gender, height, body-mass index (BMI) from electronic health or medical records of the current patient indicative of a chronic disease of the current patient. The received clinical data may additionally or alternatively include data acquired by one or more respiratory sensors, pulmonary function data, mechanical ventilator data, and so forth.

At an operation 104, the database 30 is searched using the clinical data for the current patient P as a search criterion to identify a similar patient in the database 30, such as by identifying one or more CT scan(s) 34 and/or a patient-specific mechanical ventilation model 36 for the similar patient. At an operation 106, the similar patient data S for the similar patient identified in the operation 104 is retrieved from the database 30. The similar patient data S can be, for example, a CT scan and/or a patient-specific mechanical ventilation model for the similar patient, possibly along with other data such as BMI, or other non-imaging data for the similar patient. The similar patient data S are adjusted to the current patient P, for example by adjusting the similar patient data S to account for known differences between the current patient P and the similar patient (for example, differences in BMI, weight, lung size determined from the ultrasound and/or so forth) and the adjusted similar patient data is used to construct a patient-specific mechanical ventilation model 36 for the current patient P.

In the operation 104, the similar patient can be identified in the database 30 as having, for example a nearest or most similar parameter, such as lung geometry and lung function e.g., size, shape, functional measures, and so forth), based on 2D imaging information (e.g., X-ray, US, and so forth), gender, height, BMI, electronic health or medical records, wearable data (e.g., breathing rate, physical condition, and so forth), pulmonary function tests (i.e., spirometry data), mechanical ventilator data, and so forth. A similarity search method may comprise different techniques depending on the type of data (see, e.g., E. Parimbelli, S. Marini, L. Sacchi, R. Bellazzi, 2018, "Patient similarity for precision medicine: A systematic review", Journal of Biomedical Informatics, Volume 83, 2018, Pages 87-96). In another example, a feature selection and training process can be performed. If a data set in which all patients have a lung geometrical model or a CT scan, similar geometries can be found using a suitable technique (see, e.g., US 2011/0191283 which is incorporated herein by reference). Non-CT features that best predict similar lung geometries can be subsequently determined or selected, for example with a correlation or regression method or with the help of machine learning methods.

In a first embodiment, the similar patient data S retrieved from the database 30 includes CT scan(s) 34 of the similar patient (and not a patient-specific mechanical ventilation model 36 for the similar patient). The determination operation 106 then includes an adjusting or adapting process in which the CT scan 34 for the similar patient is adjusted to the current patient P based on the received clinical data for the current patient P to generate a simulated CT scan for the current patient P. The adjusting process can include identifying at least one patient-specific dimension of the lungs of the current patient from the received clinical data for the current patient, and adjusting the CT scan 34 for the similar patient to include the at least one patient-specific dimension of the lungs of the current patient P to generate the simulated CT scan for the current patient. In one example, a size of the scale of the dimensions of the CT scan 34 can be adjusted for the similar patient to match with the dimensions of the CT scan 34 for the current patient P. The patient-specific mechanical ventilation model 36 for the current patient can then be constructed based on the simulated CT scan 34 for the current patient. In some examples, a comparison of the CT scan 34 for the similar patient and the simulated CT scan for the current patient can be displayed, either on the display device 14 of the mechanical ventilator 2, or the display device 24 of the electronic processing device 18. In another embodiment, the adjusting process can include identifying at least one patient specific feature or condition (e.g., a blocked airway, and infected region, and so forth) of the lungs of the current patient P from the received clinical data for the current patient, and adjusting the patient-specific mechanical ventilation model 36 for the current patient P.

In a second (not necessarily mutually exclusive) embodiment, the similar patient data S retrieved from the database 30 includes a patient-specific mechanical ventilation model 36 for the similar patient (and not the CT scan(s) 34). The determination operation 106 then includes an adjusting process in which the patient-specific mechanical ventilation model 36 for the similar patient can be adjusted based on the received clinical data for the current patient P to generate the patient-specific mechanical ventilation model 36 for the current patient P. The adjusting process can include identifying at least one patient-specific feature, condition, and/or dimension of the lungs of the current patient from the received clinical data for the current patient, and the patient-specific mechanical ventilation model 36 for the similar patient is adapted to include the at least one patient-specific feature, condition, and/or dimension of the lungs of the current patient to generate the patient-specific mechanical ventilation model 36 for the current patient.

In another embodiment, the received clinical data for the current patient P includes electrical impedance tomography (EIT) data for the current patient P. The determination operation 106 then includes calibrating the patient-specific mechanical ventilation model 36 for the current patient generated from the similar patient data S with the EIT data for the current patient P.

In some examples, the similar patient can have a healthy or a diseased lung. If the patient-specific mechanical ventilation model 36 is locally distorted too much due to disease, the diseased region is manually or automatically replaced with a normal tissue region (for example, bullae are replaced by normal parenchyma). A three-dimensional (3D) location, size, and/or properties of diseased or functionally impaired regions in the lungs of the current patient ["regions of interest"] from the clinical data can be determined using imaging modalities other than CT, for example with X-ray or US. This process can be supported with machine learning (see, e.g., Wang, Yifan & Zhong, Zichun & Hua, Jing. (2019). "DeepOrganNet: On-the-Fly Reconstruction and Visualization of 3D/4D Lung Models from Single-View Projections by Deep Deformation Network". IEEE Transactions on Visualization and Computer Graphics. PP. 1-1.

The adjusting or adapting processes can include adapting local boundary conditions and/or local mechanical (i.e., material) properties (e.g., block air flow, restrict deformation, or adapt the material parameters, such as on a lobe or a segment level) in the corresponding regions of the patient-specific mechanical ventilation model 36 of the similar patient.

At an operation 108, ventilator configuration data for mechanically ventilating the current patient P is generated based on the determined patient-specific mechanical ventilation model 36 for the current patient P. In some embodiments, at an operation 110, the mechanical ventilator 2 is configured for the current patient using the generated ventilator configuration data, and the configured mechanical ventilator 2 is operated to deliver mechanical ventilation to the current patient. In some examples, an uncertainty in the ventilator configuration data can be determined from a variation in current mechanical ventilation settings in a precision cohort. When the mechanical ventilation settings in this precision cohort are scattered to a large extent, the uncertainty is high, and vice versa.

Figure 3:
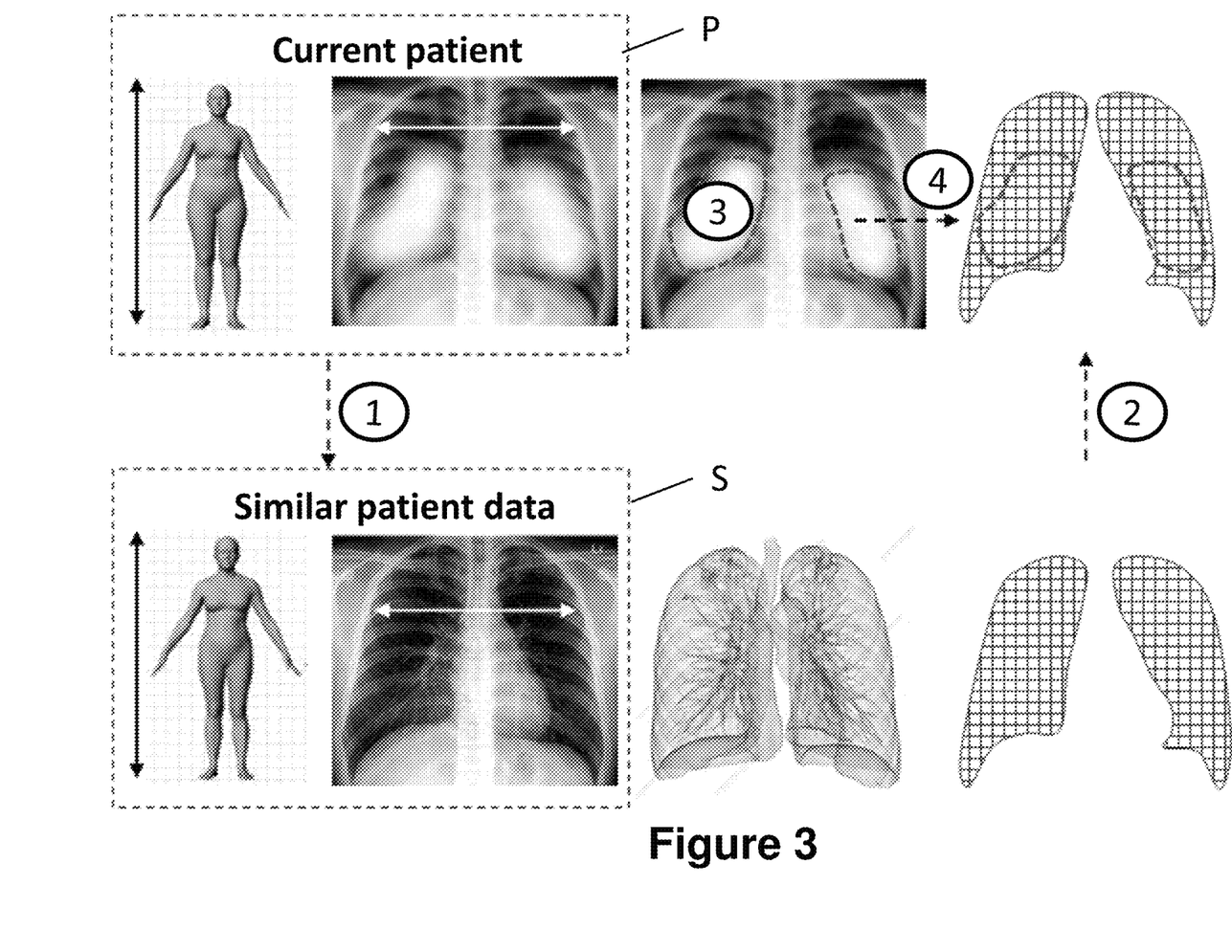
FIG. 3 diagrammatically shows the operations of the flow chart of FIG. 2.

With reference to FIG. 3, the above approach is outlined by diagrammatic steps. In an operation 1 shown in FIG. 3, the similar patient is identified (corresponding to operation 104 of FIG. 2). The operations 2, 3, and 4 then depict the adaptation 106 of the similar patient data S to generate the patient-specific ventilation model of the current patient P. In FIG. 3, the operation 2 diagrammatically denotes identifying the similar patient data S (e.g., the CT scan 34 and/or the patient-specific mechanical ventilation model 36 for the similar patent). The operation 3 diagrammatically denotes identifying regions of interest in the patient-specific ventilation model of the current patient P. The operation 4 diagrammatically denotes adjusting (if necessary) the feature, condition or overall lung size and shape of the similar patient data S to that of the current patient P. For example, the similar patient data are adapted to represent the location, size, and properties of diseased or functionally impaired regions in the lungs of the current patient P (determined from current patient data obtained using imaging modalities other than CT, for example with 2D X-ray or ultrasound).

In some embodiments, the searching operation 104 further identifies a clinical trajectory of the similar patient. For example, the clinical trajectory of the similar patient can comprise a clinical treatment trajectory of the similar patient. When a patient stays in the ICU, decisions need to be made regarding radiation imaging and regarding the adjustment of the mechanical ventilation therapy. The patient-specific mechanical ventilation model 36 which was developed initially might become outdated after a while. However, a new CT scan causes additional radiation and is a challenge with ICU patients.

Thus, it may be advantageous to avoid or to postpone a new CT scan as long as possible, while still using an up-to-date patient-specific mechanical ventilation model 36 of the current patient. For this purpose, the data trajectory of the current patient is compared with the data trajectory of the similar patient (where in this case the trajectory of the similar patient is part of the similar patient data S retrieved from the database 30). The advantage is that for the similar patient(s) the treatment decisions and outcomes are known (i.e., are prior knowledge). Therefore, the data trajectory of the similar patient(s) is a good benchmark for predicting the trajectory of the current patient P. In some examples, a rate of change in the clinical treatment trajectory can determined, and the determined rate of change can be used to predict the trajectory of the current patient P.

In this embodiment, a recommended time for updating the patient-specific mechanical ventilation model 36 for the current patient is estimated based on the clinical treatment trajectory of the similar patient. An alert can then be output (e.g., either on the display device 14 of the mechanical ventilator 2, or the display device 24 of the electronic processing device 18) indicating the patient-specific mechanical ventilation model 36 should be updated at the recommended time.

As used herein, a proximity parameter d for determining the similar patient can be indicated as "patient similarity metric, or -measure or -distance. The parameter d can be based on a single 1-dimensional measurement such as a blood pressure, or a combination of multi-dimensional measurements such as imaging, patient monitoring and mechanical ventilator data. Single and multi-dimensional patient similarity metrics are used (see, e.g., Huang H-z, Lu X-d, Guo W, Jiang X-b, Yan Z-m and Wang S-p (2021) Heterogeneous Information Network-Based Patient Similarity Search. Front. Cell Dev. Biol. 9:735687; Sharafoddini A, Dubin J A, Lee J, 2017, "Patient Similarity in Prediction Models Based on Health Data: A Scoping Review", JMIR Med Inform 2017; 5(1): e7).

In some examples, a (relative) speed with which the proximity parameter d changes can be accounted for in identifying a clinical treatment trajectory of the similar patient as $w=(dd/dt)/d$. A data trajectory is the time evolvement of a multidimensional vector x which defines the condition or the disease state of the current patient. The data includes clinical data such as bedside imaging data, mechanical ventilator data, patient monitoring data, but also the patient-specific mechanical ventilation model 36 of the similar patient) and CT imaging. A change in the disease state is indicated as Dx. In addition, a (relative) speed with which the disease state changes can accounted for in identifying a clinical treatment trajectory of the similar patient as $v=(Dx/dt)/x$.

At a time $t=0$ ($t_0$), the similar patient is searched, and the proximity parameter d is calculated using a patient similarity analysis, taking as input all the available data. From to onwards, the four parameters (d, w) and (Dx, v) can be calculated. Based on the four parameters (d, w) and (Dx, v), a decision, advise or action is generated and provided. The process can be implemented in the form of a decision tree, a flow chart or a look-up table which provides an advice or an action. Alternatively, a dashboard may present and compare the clinical data, treatments and outcomes of the current and the similar patient(s). The dashboard could also indicate the confidence we have in the result of a prediction, (e.g., be showing an ensemble of future trajectories for different similar patients).

When the four parameters (d, w) and (Dx, v) are small, for example <10%, meaning that the condition of the similar patient stays close to the current patient and there is no major or rapid change in the disease state, there is no reason to assume that the patient-specific mechanical ventilation model 36 predictions of the index patient are no longer valid, and it is advised to maintain the patient-specific mechanical ventilation model 36 of the current patient which was constructed at $t_0$. The ventilation therapy and settings are maintained and there is no need to order a new CT scan.

When there is a change in the disease state (Dx), and the current patient stays close to the similar patient, the prior knowledge from the similar patient can be used. For example, it turned out that the similar patient did not need a new CT scan. In such case it might be sufficient to rework the patient-specific mechanical ventilation model 36 of the current patient.

On the other hand, when the similar patient needed a new CT scan and accordingly a new the patient-specific mechanical ventilation model 36 was developed, it can be advised to import the new the patient-specific mechanical ventilation model 36 of the similar patient and personalize this the patient-specific mechanical ventilation model 36 using the data of the current patient.

When there is a change in the disease state (Dx), and the proximity of the similar patient(s) is large and/or increasing, for example (d, w)>10%, it may be advised to take a new CT scan for the current patient and develop a new the patient-specific mechanical ventilation model 36, because the confidence in both the old patient-specific mechanical ventilation model 36 of the current patient and the patient-specific mechanical ventilation model 36 of a similar patient is low.

When a similar patient had a negative outcome, and a CT scan could have been beneficial, the patient-specific mechanical ventilation model 36 can be updated sooner. Based on the updated the patient-specific mechanical ventilation model 36 simulations, the ventilation therapy can be adjusted.

Besides monitoring the data of the current patient and the selected similar patient, the proximity $d_N$ of N other patients can be monitored (in which case the similar patient search runs continuously). When a third patient comes closer to the current patient then the initial similar patient, $d_3<d$, the data of the third patient can be used. When there is a cluster of N patients close to the index patient, $d_N<10\%$, the treatment and outcome data of this precision cluster can be used in the decision.

Based on the proximity (d,w) and the data trajectory (x, v), many different actions or decisions can be defined. If the four variables can take a high and a low value, there are in total $2^4=16$ possible combinations. Each combination can represent a different clinical situation, and accordingly a specific decision, advice, or action. This can be implemented in an extended look-up table. Expert knowledge or learning can help to define the situations and the corresponding decision, advise, or action.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A non-transitory storage medium storing instructions readable and executable by at least one electronic processor to:
   receive clinical data for a current patient (P);
   search a database of CT scans and/or patient-specific mechanical ventilation models for other patients using the clinical data for the current patient as a search criterion to identify a similar patient in the database and similar patient data(S) comprising a CT scan and/or a patient-specific mechanical ventilation model for the similar patient;
   determine a patient-specific mechanical ventilation model for the current patient based on the CT scan and/or patient-specific mechanical ventilation model for the similar patient; and
   generate ventilator configuration data for mechanically ventilating the current patient based on the determined patient-specific mechanical ventilation model for the current patient;
   configure a mechanical ventilator for the current patient using the generated ventilator configuration data; and
   operate the configured mechanical ventilator to deliver mechanical ventilation to the current patient.

2. The non-transitory storage medium of claim 1, wherein the received clinical data for the current patient includes imaging data of lungs of the current patient, and the imaging data of the lungs of the current patient does not include a computed tomography (CT) scan of the lungs of the current patient.

3. The non-transitory storage medium of claim 2, wherein the imaging data of the lungs of the current patient consists of two-dimensional (2D) X-ray imaging data or ultrasound imaging data.

4. The non-transitory storage medium of claim 1, wherein the received clinical data for the current patient includes clinical data indicative of one or more of: lung size, lung shape, lung function, gender, height, body-mass index (BMI), data from electronic health or medical records of the current patient indicative of a chronic disease of the current patient, data acquired by one or more respiratory sensors, pulmonary function data, and/or mechanical ventilator data.

5. The non-transitory storage medium of claim 1, wherein the CT scan and/or patient-specific mechanical ventilation model for the similar patient includes a CT scan for the similar patient but not a patient-specific mechanical ventilation model for the similar patient, and the determination of the patient-specific mechanical ventilation model for the current patient includes:
   adjusting the CT scan for the similar patient based on the received clinical data for the current patient to generate a simulated CT scan for the current patient; and
   constructing the patient-specific mechanical ventilation model for the current patient based on the simulated CT scan for the current patient.

6. The non-transitory storage medium of claim 5, wherein the adjusting includes:
   identifying at least one patient-specific dimension of the lungs of the current patient from the received clinical data for the current patient; and
   adjusting the CT scan for the similar patient to include the at least one patient-specific dimension of the lungs of the current patient to generate the simulated CT scan for the current patient.

7. The non-transitory storage medium of claim 5, wherein the adjusting includes:
   identifying at least one patient-specific feature and/or condition of the lungs of the current patient from the received clinical data for the current patient; and
   adjusting the patient-specific mechanical ventilation model for the similar patient to include the at least one patient-specific feature and/or condition of the lungs of the current patient to generate the patient-specific mechanical ventilation model for the current patient.

8. The non-transitory storage medium of claim 5, wherein the instructions are readable and executable by at least one electronic processor to further:
   display a comparison of the CT scan for the similar patient and the simulated CT scan for the current patient.

9. The non-transitory storage medium of claim 1, wherein the CT scan and/or patient-specific mechanical ventilation model for the similar patient includes a patient-specific mechanical ventilation model for the similar patient, and the determination of the patient-specific mechanical ventilation model for the current patient includes:
   adjusting the patient-specific mechanical ventilation model for the current patient based on the received clinical data for the current patient to generate the patient-specific mechanical ventilation model for the current patient based on the simulated CT scan for the current patient.

10. The non-transitory storage medium of claim 9, wherein the adjusting includes:
    identifying at least one patient-specific feature, condition, and/or dimension of the lungs of the current patient from the received clinical data for the current patient; and adapting the patient-specific mechanical ventilation model for the similar patient to include the at least one patient-specific feature, condition, and/or dimension of the lungs of the current patient to generate the patient-specific mechanical ventilation model for the current patient.

11. The non-transitory storage medium of claim 1, wherein the received clinical data for the current patient includes electrical impedance tomography (EIT) data for the current patient, and the determination of the patient-specific mechanical ventilation model for the current patient based on the CT scan and/or patient-specific mechanical ventilation model for the similar patient further includes:
   calibrating the patient-specific mechanical ventilation model for the current patient with the EIT data for the current patient.

12. The non-transitory storage medium of claim 1, wherein the search further identifies a clinical trajectory of the similar patient, and wherein the instructions readable and executable by at least one electronic processor further include:
   estimating a recommended time for updating the patient-specific mechanical ventilation model for the current patient based on the clinical trajectory of the similar patient; and
   outputting an alert indicating the patient-specific mechanical ventilation model should be updated at the recommended time.

13. The non-transitory storage medium of claim 1, wherein the patient-specific mechanical ventilation model for the current patient comprises an anatomical model or an artificial neural network (ANN).

14. A mechanical ventilation method comprising, with at least one electronic controller:
   receiving clinical data for a current patient (P);
   searching a database of CT scans and/or patient-specific mechanical ventilation models for other patients using the clinical data for the current patient as a search criterion to identify a similar patient in the database and similar patient data(S) comprising a CT scan and/or a patient-specific mechanical ventilation model for the similar patient;
   determining a patient-specific mechanical ventilation model for the current patient based on the CT scan and/or patient-specific mechanical ventilation model for the similar patient; and
   generating ventilator configuration data for mechanically ventilating the current patient based on the determined patient-specific mechanical ventilation model for the current patient;
   configuring a mechanical ventilator for the current patient using the generated ventilator configuration data; and
   operating the configured mechanical ventilator to deliver mechanical ventilation to the current patient.

* * * * *